(12) United States Patent
Kiel et al.

(10) Patent No.: US 7,550,628 B2
(45) Date of Patent: Jun. 23, 2009

(54) PROCESS FOR PREPARING PHENOLIC ACID SALTS OF GABAPENTIN

(75) Inventors: Jeffrey S. Kiel, Gainesville, GA (US); H. Greg Thomas, Villa Rica, GA (US); Narasimhan Mani, Port Jefferson, NY (US)

(73) Assignee: Kiel Laboratories, Inc., Gainesville, GA (US)

( * ) Notice: Subject to any disclaimer, the term of this patent is extended or adjusted under 35 U.S.C. 154(b) by 723 days.

(21) Appl. No.: 10/806,022

(22) Filed: Mar. 22, 2004

(65) Prior Publication Data

US 2004/0192617 A1 Sep. 30, 2004

Related U.S. Application Data

(60) Provisional application No. 60/457,431, filed on Mar. 25, 2003.

(51) Int. Cl.
C07C 61/08 (2006.01)
A61K 31/195 (2006.01)
(52) U.S. Cl. ........................... 562/507; 514/561
(58) Field of Classification Search ............... 560/122; 514/554, 561; 562/507
See application file for complete search history.

(56) References Cited

U.S. PATENT DOCUMENTS

| | | | |
|---|---|---|---|
| 2,397,799 A | | 4/1946 | Martin et al. |
| 2,421,714 A | | 6/1947 | Rieveschl |
| 2,950,309 A | | 8/1960 | Cavallito |
| 3,282,789 A | | 11/1966 | Marty et al. |
| 4,024,175 A | * | 5/1977 | Satzinger et al. ............ 560/122 |
| 4,309,989 A | | 1/1982 | Fahim |
| 4,552,899 A | | 11/1985 | Sunshine et al. |
| 4,619,934 A | | 10/1986 | Sunshine et al. |
| 4,749,697 A | | 6/1988 | Sunshine et al. |
| 4,749,711 A | | 6/1988 | Sunshine et al. |
| 4,749,721 A | | 6/1988 | Sunshine et al. |
| 4,749,722 A | | 6/1988 | Sunshine et al. |
| 4,749,723 A | | 6/1988 | Sunshine et al. |
| 4,767,402 A | | 8/1988 | Kost et al. |
| 4,839,354 A | | 6/1989 | Sunshine et al. |
| 5,025,019 A | | 6/1991 | Sunshine et al. |
| 5,068,413 A | | 11/1991 | Steiner et al. |
| 5,095,148 A | | 3/1992 | Mettler et al. |
| 5,132,451 A | | 7/1992 | Jennings et al. |
| 5,164,398 A | | 11/1992 | Sims et al. |
| 5,560,933 A | | 10/1996 | Soon-Shiong et al. |
| 5,599,846 A | | 2/1997 | Chopdekar et al. |
| 5,614,178 A | | 3/1997 | Bloom et al. |
| 5,663,415 A | * | 9/1997 | Chopdekar et al. ............ 560/68 |
| 5,759,579 A | | 6/1998 | Singh et al. |
| 5,948,414 A | | 9/1999 | Wiersma |
| 6,037,358 A | * | 3/2000 | Gordziel ............ 514/357 |
| 6,063,770 A | | 5/2000 | Falcon |
| 6,083,490 A | | 7/2000 | Ellis et al. |
| 6,117,452 A | | 9/2000 | Ahlgren et al. |
| 6,187,315 B1 | | 2/2001 | Falcon |
| 6,248,363 B1 | * | 6/2001 | Patel et al. ............ 424/497 |
| 6,287,597 B1 | | 9/2001 | Gordziel |
| 6,306,904 B1 | | 10/2001 | Gordziel |
| 6,383,471 B1 | | 5/2002 | Chen et al. |
| 6,403,119 B2 | | 6/2002 | Oppenheim et al. |
| 6,417,206 B1 | | 7/2002 | Leflein et al. |
| 6,462,094 B1 | | 10/2002 | Dang et al. |
| 6,509,492 B1 | | 1/2003 | Venkataraman |
| 6,703,044 B1 | | 3/2004 | Pinhasi et al. |
| 6,740,312 B2 | | 5/2004 | Chopin et al. |
| 2003/0077321 A1 | * | 4/2003 | Kiel et al. ............ 424/465 |
| 2004/0192616 A1 | * | 9/2004 | Kiel et al. ............ 514/23 |
| 2004/0192618 A1 | * | 9/2004 | Kiel et al. ............ 514/23 |

OTHER PUBLICATIONS

Gould P., Internatioanl Journal of Pharmaceutics, 33, (1986) pp. 201-217.*
Berge et a l, Journal of Pharmaceutical Sciences, vol. 66, No. 1, Jan. 1977, p. 1-18.*
Cypress Pharmaceutical, Inc., "R-Tannic-S A/D," RX Only, Cypress Pharmaceutical, Inc., (Madison, MS), p. 1, 2 (Mar. 1, 2001).
DSC Laboratories, "Phenylephrine Tannate/Pyrilamine Tannate Suspension," RX Only, DSC Laboratories (Muskegon, MI), p. 1, 2 (Aug. 1, 2001).
Ronald Goldberg, M.D. and Franklin Shuman, M.D., "Evaluation of a Prolonged Action Oral Antihistaminic Preparation as Treatment for Allergic Disorders," Clinical Report, Clinical Medicine (Washington), vol. 72 (No. 9), pp. 1475-1479 (Sep. 1, 1965).
John Weiler, M.D. et al., "Randomized, double-blind, parallel groups, placebo-controlled study of efficacy and safety of Rynatan in the treatment of allergic rhinitis using an acute model," Annals of Allergy, ACAI (Iowa City, IA), vol. 64 (No. 1), p. 63-67 (Jan. 1, 1990).
Berge et al. Pharmaceutical Salts. Journal of Pharmaceutical Sciences, Jan. 1977, vol. 66, No. 1, pp. 1-19.

* cited by examiner

*Primary Examiner*—Taylor Victor Oh
(74) *Attorney, Agent, or Firm*—King & Schickli, PLLC

(57) ABSTRACT

The present invention provides a novel process for preparation of the tannate salt of gabapentin for human and veterinary pharmaceutical use. Tannate salts of active pharmaceutical ingredients are used in sustained release applications and to improve certain organoleptic properties such as taste. However, the prior art neither discloses nor suggests the preparation of gabapentin tannate. The process for preparing gabapentin tannate includes the mixing of gabapentin and tannic acid together in the presence of one or more solvents. The method may further include the step of selecting the one or more solvents from a group consisting of purified water, ethanol, glycerin, propylene glycol, diethylether, methylene chloride, acetone, isopropyl alcohol and mixtures thereof. The process may also include the steps of isolating and purifying the tannate salt. This may be accomplished by filtration, drying, centrifugation and lyophilization. The process may utilize either natural or synthetic tannic acid.

15 Claims, No Drawings

PROCESS FOR PREPARING PHENOLIC ACID SALTS OF GABAPENTIN

This application claims the benefit of U.S. Provisional patent application Ser. No. 60/457,431 filed on Mar. 25, 2003.

TECHNICAL FIELD

The present invention relates generally to the field of tannate chemistry and, more particularly, to the compound gabapentin tannate.

BACKGROUND OF THE INVENTION

The literature describes many ways of preparing gabapentin from a variety of starting materials, but there is no suggestion of the preparation of gabapentin tannate. U.S. Pat. No. 4,024,175 describes at least three methods of preparing gabapentin from cyclohexyl-1, 1-diacetic acid. Each of these methods results in the formation of gabapentin hydrochloride salt, which may be converted to I-(aminomethyl)-I-cyclohexaneacetic acid by treatment with a basic ion exchanger and then crystallized from a solvent such as ethanol/ether.

The prior art neither discloses nor suggests the preparation of gabapentin tannate. The formation of a tannate salt of gabapentin is unexpected because of the close proximity of a carboxylic acid group to the amine group. The negative charge on the carboxylic acid group was expected to shield and possibly neutralize the positive charge on the proximal nitrogen. Since tannate salts are thought to normally form through an ionic interaction with a positively charged amine functional group, the close proximity of the carboxylic acid group was expected to prevent the formation of the tannate salt.

SUMMARY OF THE INVENTION

In accordance with the object of the present invention a process for preparing the novel and useful chemical compound gabapentin tannate is provided. Further, a chemical composition comprising gabapentin tannate is provided. The process for preparing gabapentin tannate may be further described as comprising the mixing of gabapentin and tannic acid together in the presence of a solvent. The method may further include the step of selecting the one or more solvents from a group consisting of purified water, ethanol, glycerin, propylene glycol, diethylether, methylene chloride, acetone, isopropyl alcohol and mixtures thereof.

The process may also include the steps of isolating and purifying the tannate salt. This may be accomplished by filtration, drying, centrifugation and lyophilization.

Naturally occurring tannic acid comprises a mixture of compounds. They are considered to be secondary metabolites, with a molecular weight of 500-5000 Da, that have no specific metabolic function. As with many natural polymers, a rigorous chemical definition of tannins is difficult.

Hydrolyzable tannins are molecules with a polyol (generally D-glucose) as a central core, with the hydroxyl groups of the carbohydrate partially or totally esterified with phenolic groups. They derive their name from their propensity to be hydrolyzed by mild acids or mild bases to yield carbohydrates and phenolic acids. Synthetic tannic acid may comprise a purified form of any of the components of naturally occurring tannic acid.

The present invention may utilize tannic acid of either a natural or synthetic source. The term "tannic acid" herein refers to either natural or synthetic tannic acid as described above.

DETAILED DESCRIPTION OF THE INVENTION

The present invention relates to a novel compound and composition comprising gabapentin tannate as well as a novel method of synthesizing the tannate salt of the active pharmaceutical ingredient (API) gabapentin. Gabapentin is a neuroleptic agent indicated as adjunctive therapy in the treatment of partial seizures, with and without secondary generalization, in adults with epilepsy, faintness attacks, hypokinesis, pain associated with shingles and cranial traumas. Gabapentin is a white to off-white crystalline solid and is a polymorphic substance. It is freely soluble in water and across a wide range of pH and is characterized by a marked bitter taste. Chemically, gabapentin is 1-(amino methyl) cyclohexaneacetic acid with the empirical formula $C_9H_{17}NO_2$ and a MW of 171.24. Typically gabapentin is administered in multiple doses for optimal pharmacological action.

The literature describes many ways of preparing gabapentin from a variety of starting materials, but there is no suggestion of the preparation of gabapentin tannate. U.S. Pat. No. 4,024,175 describes at least three methods of preparing gabapentin from cyclohexyl-1, 1-diacetic acid. Each of these methods results in the formation of gabapentin hydrochloride salt, which may be converted to I-(aminomethyl)-I-cyclohexaneacetic acid by treatment with a basic ion exchanger and then crystallized from a solvent such as ethanol/ether.

There is no mention or suggestion of preparing gabapentin tannate in the prior art. The formation of a tannate salt of gabapentin is unexpected because of the close proximity of a carboxylic acid group to the amine group. The negative charge on the carboxylic acid group was expected to shield and possibly neutralize the positive charge on the proximal nitrogen. Since tannate salts are thought to normally form through an ionic interaction with a positively charged amine functional group, the close proximity of the carboxylic acid group was expected to prevent the formation of the tannate salt.

Naturally occurring tannic acid comprises a mixture of compounds. They are considered to be secondary metabolites, with a molecular weight of 500-5000 Da, that have no specific metabolic function. They are complex phenol-rich polymers found in many foods. As with many natural polymers, a rigorous chemical definition of tannins is difficult. In general two classes are distinguished—the hydrolyzable and the condensed tannins. Hydrolyzable tannins or tannic acids are referenced in the various pharmacopeias and are composed of gallic acid or its condensation product ellagic acid esterified to the hydroxyl groups of glucose.

Hydrolyzable tannins are molecules with a polyol (generally D-glucose) as a central core, with the hydroxyl groups of the carbohydrate partially or totally esterified with phenolic groups. They derive their name from their propensity to be hydrolyzed by mild acids or mild bases to yield carbohydrates and phenolic acids. Synthetic tannic acid may comprise a purified form of any of the components of naturally occurring tannic acid.

The present invention may utilize tannic acid of either a natural or synthetic source. The term "tannic acid" herein refers to either natural or synthetic tannic acid as described above.

Tannate salts have been found to have better organoleptic properties such as taste in comparison to other salts or free base forms. In comparison to typical salt forms, the tannate salt of the active pharmaceutical ingredient (API) is a significantly larger molecule that is typically less soluble, which affords absorption of the API over prolonged intervals of time, reducing the frequency of administration and thereby improving patient compliance.

Traditionally, a tannate salt is prepared by reacting the free base of the API with tannic acid in the presence of a volatile solvent, usually isopropanol or water, for designated times and temperatures. After the completion of the reaction, the mixture is filtered, washed and vacuum dried to obtain the tannate salt. The conditions required by the prior art for the isolation of the tannate salt often lead to decreased yield and purity. The yield of the products using such methods varies from about 70% when using the isopropanol route to 90-97% using the water method. The purity of the tannate salt produced as described above is variable. The purity ranges from 85-90% using the isopropanol route to about 90-98% using the water route.

The formation of the tannate salt is by the reaction of the amine groups (in the 1°, 2°, 3°, 4° configuration) or of other basic functional groups with the carboxylic and hydroxyl groups present in tannic acid. For example, the amine groups of the API could react covalently with the hydroxyl groups of tannic acid by an oxime formation or by the ionization of the tannic acid and the protonation of the nitrogen atom in the amine group facilitating an ionic interaction. In the present invention the active ingredient gabapentin is present in zwitter-ionic form. The protonated nitrogen reacts with tannic acid to form the tannate salt. The formation of a tannate salt of gabapentin is unexpected because of the close proximity of a carboxylic acid group to the amine group. The negative charge on the carboxylic acid group was expected to shield and possibly neutralize the positive charge on the proximal nitrogen. Since tannate salts are thought to normally form through an ionic interaction with a positively charged amine functional group, the close proximity of the carboxylic acid group was expected to prevent the formation of the tannate salt.

More specifically describing the present process of preparing gabapentin tannate, the mixing step further includes adding the gabapentin to a solvent and then adding tannic acid to gabapentin and the solvent. Alternatively, the mixing step may include adding the tannic acid to a solvent and then adding gabapentin to the tannic acid and the solvent. In yet another alternative the mixing step may be described as including the mixing of gabapentin and tannic acid powders together and then the adding of a solvent. Still further, the mixing may include adding gabapentin to a solvent to create a first reaction mixture, adding tannic acid to a solvent to create a second reaction mixture and mixing together the two reaction mixtures.

Still further the process may be described as including the additional requirement of maintaining a pH of between about 2 and about 11 during the conversion. Additionally, the method may be further described as including the requirement that the weight ratio of tannic acid to gabapentin be between about 0.1:1 to about 10:1 so that the tannic acid is present at about 0.05 to about 40.0% by weight in the reaction mixture.

The process may also include the steps of isolating and purifying the tannate salt. This may be accomplished by filtration, drying, centrifugation and lyophilization.

The invention will further be described by means of the following examples, which illustrate the synthesis of gabapentin tannate.

EXAMPLE 1

Formation of the Insoluble Tannate Salt—Dispersion Method—I

| Ingredient | Amount (g) |
| --- | --- |
| Gabapentin | 40.000 |
| Tannic acid | 48.000 |
| Purified water | 450 ml |

The conversion process used in this example to synthesize gabapentin tannate is done at room temperature as follows. About 150 ml of purified water is placed in a suitable vessel and gabapentin is added to the water and stirred to form a solution. 300 ml of purified water is placed in the bowl of a planetary mixer. While mixing the water, tannic acid is added and mixing is continued to form a solution. While mixing the tannic acid solution, the solution of gabapentin is added slowly. Once all of the gabapentin solution is added, mixing is continued for 10-15 minutes. The synthesis yields gabapentin tannate as a precipitated salt. The ratio of tannic acid to gabapentin used in this example is 1.2:1. The salt is then recovered by filtration and drying.

The completeness of the reaction and the formation of the tannate salt were followed by taking samples at different stages of the conversion process. Due to the large size of the tannate salt, it usually precipitates from solution upon formation. The absence or loss of gabapentin from solution is correlated with the formation of the tannate salt.

EXAMPLE 2

Formation of the Insoluble Tannate Salt—Dispersion Method—II

| Ingredient | Amount (g) |
| --- | --- |
| Gabapentin | 40.000 |
| Tannic acid | 32.000 |
| Purified water | 250 ml |
| Ethanol | 50 ml |

The conversion process used in this example to synthesize the tannate salt of gabapentin is done at room temperature as follows: 250 ml of purified water and 50 ml of ethanol are placed in a beaker. While mixing the water/ethanol mixture, tannic acid is added and mixing is continued to form a solution. While mixing the tannic acid solution, gabapentin powder is added slowly. The gabapentin reacts with the tannic acid to form the tannate salt. Since the tannate salt has low solubility, it is precipitated from solution and can be isolated by centrifugation. The ratio of tannic acid to gabapentin used is 0.8:1.

The completeness of the reaction and the formation of the tannate salt can be followed as described in Example 1.

EXAMPLE 3

Formation of the Insoluble Tannate Salt—Dry Powder Method—I

| Ingredient | Amount (g) |
| --- | --- |
| Gabapentin | 88.24 |
| Tannic acid | 88.24 |
| Purified water | 150 ml |

The conversion process used in this example to prepare the tannate salt of the active is performed at room temperature using the following procedure. About 150 ml of purified water is placed in a suitable vessel and gabapentin is added to the water and stirred to dissolve. Tannic acid powder is placed in a suitable planetary mixer and mixed. The solution of gabapentin is added to tannic acid while mixing, to generate the gabapentin tannate. The ratio of tannic acid to gabapentin used is 1:1. Experiments similar to those used to assay formation of the tannate salt in examples 1 and 2 can be applied to this example as well.

EXAMPLE 4

Formation of the Insoluble Tannate Salt—Dry Powder Method—II

| Ingredient | Amount (g) |
|---|---|
| Gabapentin | 88.24 |
| Tannic acid | 176.48 |
| Purified water | 100 ml |

The conversion process used in this example to synthesize the tannate salt of the active is performed at room temperature using the following procedure. Gabapentin and tannic acid are placed in a suitable planetary mixer or blender and mixed for a period of 10 minutes to obtain a powder blend. 100 m of purified water is added onto the powders while mixing, to generate the tannate salt of gabapentin. This synthetic process yields gabapentin tannate salt as a uniformly distributed, lump free powder mass.

The ratio of tannic acid to gabapentin used is 1:2. Experiments similar to those used to assay formation of the tannate salt in examples 1 and 2 can be applied to this example as well.

EXAMPLE 5

Formation of the Insoluble Tannate Salt—Dry Powder Method—III

| Ingredient | Amount (g) |
|---|---|
| Gabapentin | 88.24 |
| Tannic acid | 176.48 |

The conversion process used in this example to synthesize the tannate salt of the active is performed at room temperature using the following procedure. Gabapentin and tannic acid are placed in a suitable planetary mixer or blender and mixed at a temperature of 95 degrees C. Mixing is continued for 30 minutes at the high temperature to prepare gabapentin tannate.

The ratio of tannic acid to gabapentin used is 1:2. Experiments similar to those used to assay formation of the tannate salt in examples 1 and 2 can be applied to this example as well.

It should be understood that the above examples are illustrative of several different embodiments of the invention herein disclosed. Given the present disclosure, it is anticipated that numerous variations will be devised by those skilled in the art without departing from the spirit and scope of the present invention. Latitude of modification, substitution and change is intended and in some instances, some features of the invention will be employed without a corresponding use of other features. Accordingly, it is intended that the spirit and scope of the invention disclosed herein should be limited only by the following claims.

What is claimed is:

1. A process for preparing gabapentin tannate, comprising: mixing gabapentin and tannic acid to obtain gabapentin tannate wherein the tannic acid component is of either natural or synthetic origin, and wherein said gabapentin and said tannic acid are mixed together while maintaining a temperature of between about 15 to about 150 degrees C.

2. A process for preparing gabapentin tannate, comprising: mixing gabapentin and tannic acid to obtain gabapentin tannate wherein the tannic acid component is of either natural or synthetic origin, and wherein the weight ratio of said tannic acid to said gabapentin is between about 0.1:1 to about 10:1.

3. A process for preparing gabapentin tannate, comprising: mixing gabapentin and tannic acid to obtain gabapentin tannate wherein the tannic acid component is of either natural or synthetic origin, and wherein said mixing is performed while maintaining a pH of between about 2 to about 11.

4. The process of claim 1, further comprising the step of isolating and purifying the gabapentin tannate.

5. The process of claim 4, wherein said isolating and purifying is performed by a procedure selected from a group consisting of filtering, drying, centrifuging, and lyophilizing.

6. The process of claim 1, wherein the gabapentin and tannic acid are mixed together in the presence of a solvent, and wherein the solvent is selected from a group consisting of purified water, ethanol, glycerin, propylene glycol, diethylether, methylene chloride, acetone, isopropyl alcohol, and mixtures thereof; and isolating and purifying the gabapentin tannate.

7. The process of claim 6, wherein said isolating and purifying step is performed by a procedure selected from a group consisting of filtering, drying, centrifuging, and lyophilizing.

8. The process of claim 2, further comprising the step of isolating and purifying the gabapentin tannate.

9. The process of claim 8, wherein said isolating and purifying is performed by a procedure selected from a group consisting of filtering, drying, centrifuging, and lyophilizing.

10. The process of claim 3, further comprising the step of isolating and purifying the gabapentin tannate.

11. The process of claim 10, wherein said isolating and purifying is performed by a procedure selected from a group consisting of filtering, drying, centrifuging, and lyophilizing.

12. The process of claim 2, wherein the gabapentin and tannic acid are mixed together in the presence of a solvent, and wherein the solvent is selected from a group consisting of purified water, ethanol, glycerin, propylene glycol, diethylether, methylene chloride, acetone, isopropyl alcohol, and mixtures thereof; and isolating and purifying the gabapentin tannate.

13. The process of claim 12, wherein said isolating and purifying step is performed by a procedure selected from a group consisting of filtering, drying, centrifuging, and lyophilizing.

14. The process of claim 3, wherein the gabapentin and tannic acid are mixed together in the presence of a solvent, and wherein the solvent is selected from a group consisting of purified water, ethanol, glycerin, propylene glycol, diethylether, methylene chloride, acetone, isopropyl alcohol, and mixtures thereof; and isolating and purifying the gabapentin tannate.

15. The process of claim 14, wherein said isolating and purifying step is performed by a procedure selected from a group consisting of filtering, drying, centrifuging, and lyophilizing.

* * * * *